(12) United States Patent
Knoblauch et al.

(10) Patent No.: US 7,956,092 B2
(45) Date of Patent: Jun. 7, 2011

(54) NON-TOXIC INSECTICIDE

(75) Inventors: Cathy Knoblauch, Whitecourt (CA); Ken Fry, Calgary (CA)

(73) Assignee: Alberta Innovates—Technology Futures, Edmonton, Alberta (CA)

(*) Notice: Subject to any disclaimer, the term of this patent is extended or adjusted under 35 U.S.C. 154(b) by 366 days.

(21) Appl. No.: 12/101,655

(22) Filed: Apr. 11, 2008

(65) Prior Publication Data

US 2009/0258950 A1 Oct. 15, 2009

(51) Int. Cl.
*A01N 37/00* (2006.01)
*A01N 35/00* (2006.01)
*A01N 31/00* (2006.01)
*A01N 27/00* (2006.01)
*A01N 65/00* (2006.01)

(52) U.S. Cl. ........ 514/558; 514/701; 514/724; 514/762; 424/725

(58) Field of Classification Search .................. 514/558, 514/701, 724, 762; 424/725
See application file for complete search history.

(56) References Cited

U.S. PATENT DOCUMENTS

2005/0244445 A1* 11/2005 Anderson .................. 424/405

OTHER PUBLICATIONS

Wikipedia, The Free Encyclopedia; Pyrethrin; http://en/wikipedia/wiki/Pyrethrin; Internet; Oct. 29, 2010.
U.S. Department of Health and Human Service, Food and Drug Administration; Guidance for Industry: Frequently Asked Questions About GRAS; http://www/cfsan.fda.gov/guidance.htm; Internet; Dec. 2004.
Code of Federal Regulations; Substances Generally Recognized as Safe; 21 CFR Part 182; Sep. 22, 2010.
Code of Federal Regulations; Direct Food Substances Affirmed as Generally Recognized as Safe; 21 CFR Part 194; Sep. 22, 2010.
Code of Federal Regulations; Indirect Food Substances Affirmed as Generally Recognized as Safe; 21 CFR Part 186; Sep. 22, 2010.

* cited by examiner

*Primary Examiner* — Raymond J Henley, III
(74) *Attorney, Agent, or Firm* — Bennett Jones LLP

(57) ABSTRACT

A non-toxic insecticidal composition includes a base horticultural oil, an emulsifier such as potassium salts of fatty acids, cinnamaldehyde and eugenol.

14 Claims, 2 Drawing Sheets

NON-TOXIC INSECTICIDE

FIELD OF THE INVENTION

The present invention relates to non-toxic insecticidal compositions.

BACKGROUND

Commercially available insecticides for home and professional use, commonly include active ingredients which are poisonous to not only the target insect, but also humans and household pets, when exposed in high enough concentrations, or in confined spaces. Adverse side effects or intoxication may occur, and may be exacerbated in more sensitive persons, or persons with reduced body mass, such as children.

There have been efforts to develop insecticides, particularly those that are intended for home use, which are effective in controlling targeted insects, but are non-toxic to humans and pets. Unfortunately, non-poisonous insecticides have not demonstrated real efficacy. They may be cost-prohibitive, inadequately lethal to the targeted insects, or too slow-acting.

The Environmental Protection Agency (EPA) regulates the use of potentially toxic ingredients in pesticidal compositions under the Federal Insecticide, Fungicide and Rodenticide Act in the United States. Certain materials considered to be either active or inert materials by the EPA have been deregulated or otherwise identified as acceptable "safe" substances offering minimum risk in normal use. Other materials are currently undergoing investigation and may be deregulated in due course. Deregulated substances are generally considered non-toxic by the consumer. Thus, the term "non-toxic" as used herein is intended to convey a composition that, while highly effective in killing targeted insect pests, is safe to use around humans, particularly small children, and pets. Essential oils are deregulated by the EPA, and include cornmint oil, cedar oil, cinnamon oil, citronella oil, clove oil, corn oil, garlic oil, lemongrass oil, linseed oil, peppermint oil, rosemary oil, soybean oil and thyme oil.

Another indicator of non-toxicity is the designation "generally regarded as safe" or GRAS by the United States Food and Drug Administration. These ingredients may not meet usual test criteria for safety, but have been extensively used and have not demonstrated any harm to consumers.

SUMMARY OF THE INVENTION

The present invention relates to non-toxic insecticidal compositions. In one aspect, the invention may comprise a base horticultural oil, an emulsifier, and a combination of essential oils, including cinnamaldehyde and eugenol. The composition may be mixed with water and applied directly to insects or an infested area.

BRIEF DESCRIPTION OF THE DRAWINGS

The drawings are briefly described as follows.

DETAILED DESCRIPTION OF PREFERRED EMBODIMENTS

Figure 1:
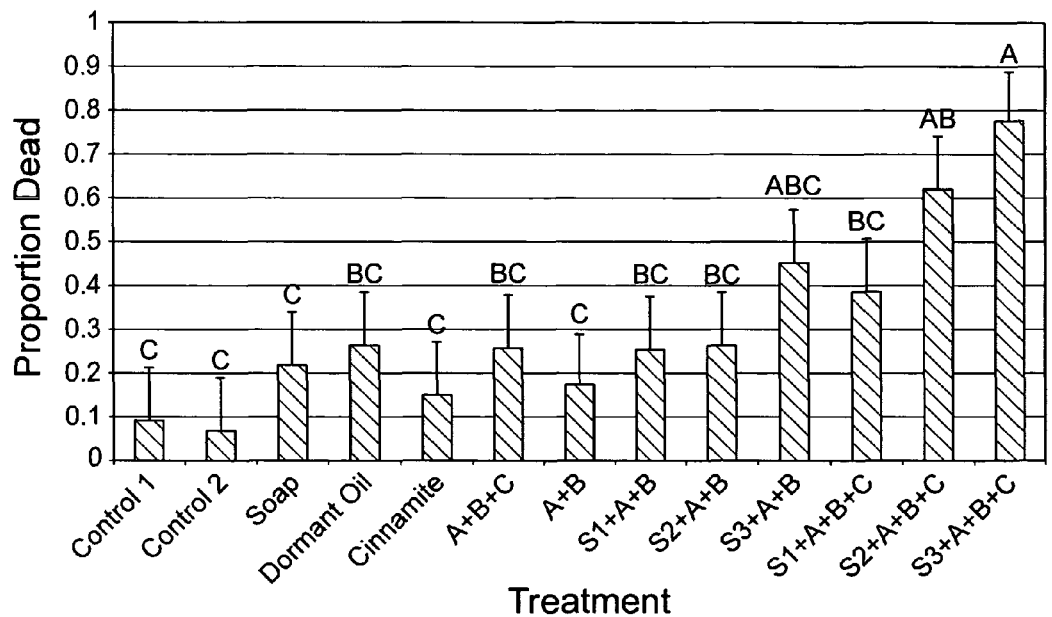
FIG. 1 is a graph showing efficacy of one embodiment of the invention against adult western flower thrips, with and without an emulsifier.

The present invention relates to non-toxic insecticidal compositions. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Generally, the invention comprises a mixture of a horticultural or dormant oil and cinnamaldehyde. Without being bound to a theory, it is believed that the horticultural oil and cinnamaldehyde act synergistically to provide effective insecticidal action. Dormant oil has been used to control pests, typically on dormant plants. Cinnamaldehyde is also reported to have some minor insecticidal activity.

In one embodiment, the horticultural oil comprises a mineral oil. Oils generally considered dormant or horticultural oils by those skilled in the horticultural arts are suitable. Dormant oils originally referred to heavier weight, less well-refined oils that were unsafe to use on plants after they broke dormancy. However, these older oils have been replaced with more refined, light-weight oils that have potential application to plant foliage. Dormant oil now refers to the time of application rather than to any characteristic type of oil. Dormant oils are used as pest control when diluted and emulsified in water, and sprayed on plants that are preferably not actively growing. The oils are believed to act by blocking air holes through which insects breathe, and disrupting the manner in which insects feed.

In one embodiment, the mineral oil has been purified to remove compounds which may be injurious to plants, such as aromatic compounds and compounds containing sulfur, nitrogen or oxygen. Vegetable oils may also be used, and in one embodiment, for example, the horticultural oil comprises cottonseed oil or soybean oil.

The horticultural oil should not be used in too great a concentration, as it may impair actively growing plants. In one embodiment, the horticultural oil may form about 0.1% to about 2.4% by volume of the composition. In one embodiment, the horticultural oil forms about 0.25% to about 1.8% by volume, and preferably about 1.2%.

In one embodiment, the horticultural oil is also mixed with at least one essential oil ingredient, and preferably a combination of two or more essential oil ingredients. In a preferred embodiment, the essential oil may comprise cinnamaldehyde or cinnamic aldehyde (or more precisely trans-cinnamic aldehyde). A preferred source of cinnamaldehyde is essential oil of cinnamon bark, which typically is about 90% cinnamaldehyde, herein referred to as cinnamon oil.

In one embodiment, the composition comprises 0.1% to about 1.2% cinnamaldehyde, or sufficient cinnamon oil to provide 0.1% to about 1.2% cinnamaldehyde. In a preferred embodiment, the composition may comprise about 0.2% to about 0.6% cinnamaldehyde.

In one embodiment, the cinnamaldehyde is used in combination with another essential oil ingredient, such as eugenol. Eugenol is the main component in clove oil and typically forms about 72% to 90% of clove oil.

In one embodiment, the composition further comprises about 0.05% to about 1.2% eugenol, or sufficient clove oil to provide 0.05% to about 1.2% eugenol. Eugenol is known to have herbicidal properties, so larger concentrations are not preferred. In a preferred embodiment, the composition comprises about 0.1% eugenol.

In one embodiment, the base oil is mixed with an emulsifier, such as, for example, potassium salts of fatty acids (PSFA), which are commonly referred to as soap salts. PSFAs are produced by adding potassium hydroxide to fatty acids found in animal fats or plant oils. Fatty acids may be extracted from various plant oils, for example, palm, coconut, olive, castor or cottonseed oil. PSFAs typically comprise potassium laurate, potassium myristate, potassium oleate and potassium ricinoleate. PSFAs are generally recognized as safe (GRAS) by the United States Food and Drug Administration.

PSFAs are also known to have insecticidal activity and are believed to act by penetrating and disrupting the lipoprotein matrix of the insect's cellular membranes, thereby dissolving the insect skin or cuticle.

In one embodiment, the PSFAs form about 0.1% to about 2% by volume of the composition. In a preferred embodiment, the PSFAs form about 0.725% to about 1.25% by volume.

The insecticidal compositions of the invention are prepared by mixing together the above components in the indicated proportions. It will be appreciated by those skilled in the art that a concentrated stock formulation can be prepared and diluted with distilled water or another inert carrier to obtain a composition with components in the desired proportions. The composition can be formulated as an aqueous or liquid flowable, suspension concentrate or any one of the conventional formulations used for insect control agents and tank mixed in the field with water or other liquid for application as a liquid spray mixture.

The compositions of the present invention may also be delivered by foams or gels or the like, using aerosol or other known delivery methods.

The above formulations may incorporate other non-active components which may be useful for a particular use, for example, adhesion agents, binders, carriers, detergents, diluents, dispersants, excipients, extenders, fillers, inorganic minerals, polymers, Theological agents, spreader sticker adjuvants, stabilizing agents, surfactants, wetting agents, propellants or combinations thereof. Components which assist in handling, administration or storage stability of the formulation are suitable. The formulations ideally should be stored in a cool, dry place where excess heat is avoided. Further, it will be appreciated that additional agriculturally acceptable active ingredients may be added and are within the scope of the invention.

In practice, the composition can be sprayed or drenched onto lawns, flower beds, gardens, pine straw, wood chips, grass, thatch, soil, leaf litter, mulch, decomposing material, or onto plants, crops or other environments where the insects are associated. Coverage of both the upper and lower leaf surfaces of plants may enhance control. Sensitive young plants and crops, or suspected nest sites may be "pretreated" before infestation occurs. The composition can also be applied to aquatic environments, standing water, damp mulch or other high moisture areas. Further, the composition can be used to control or eradicate insects associated with environments, such as greenhouses, picnic areas, backyards, parks or lakes which are frequented by humans. For example, the composition can be applied to particular environments to control insects which may be a nuisance to humans. As the composition is essentially non-toxic to humans, pets and wildlife, it can thus be used in sensitive areas where pesticide use normally causes adverse effects.

The composition can also be applied directly to insects trapped by a "sticky card" or a "bait bin," namely a covered bin containing an attractant which attracts the insects to a food source. Such sticky cards or bins are placed in areas where the insects normally frequent.

Repeated applications may be required to ensure thorough coverage, effective wetting, or replacement following environmental elements such as precipitation or wind. Applications may be made using ground or aerial application equipment. The composition is suitable for outdoor and indoor use.

The rate of application of the composition will vary on a number of factors such as, for example, the concentration of the composition, the chosen formulation, method of application, environmental conditions, extent of infestation, growth stage of the insects, and season. Overall, an effective insecticidal amount is desirable, namely an amount of the composition which is capable of controlling or eradicating the insects as measured by percent mortality or absence of further plant or crop damage. In general, the composition may be applied more frequently on plants (for example, ornamental plants) which are not consumed. Fruits and vegetables should be treated on a schedule which does not conflict with "days to harvest" or when the fruits or vegetables will be picked. Similarly, crops should be treated on a schedule which does not conflict with events such as, for example, harvesting, processing or grazing of livestock.

Generally, the compositions of the present invention are intended for broad control of many different insects. In one embodiment, the invention comprises a composition and method for controlling an insect of the orders Thysanoptera, Homoptera, Lepidopterans, or Hymenoptera. Generally, the compositions are less effective against insects having hard or protective exoskeletons, or larger insects with higher body mass to surface area ratios.

In particular, the compositions have been found to be effective against insections of the orders Thysanoptera and Homoptera. The method comprises providing a composition described above in an insecticidally effective amount, and either contacting the insect with the composition or applying the composition to an infested area. As used herein and in the claims, "insecticidally effective amount" means an amount of the composition which is capable of controlling or eradicating an insect of the order Thysanoptera or Homoptera as measured by percent mortality or absence of further plant or crop damage. "Infested area" means an area affected by insects of the order Thysanoptera or Homoptera. The term is meant to include plants, crops, lawns, flower beds, gardens, pine straw, wood chips, grass, thatch, soil, leaf litter, mulch, decomposing material, pool areas or other environments where the immature and adult insects are associated.

The order Thysanoptera or "thrips" is an extensive order (5,500 species) of tiny, slender insects with fringed wings. Approximately fifty species within the families Thripidae and Phlaeothripidae are considered pests. Thrips predominantly feed on commercially valuable plants and crops (sources of sap, juice and water), resulting in deformities, defoliation, scarring and loss of yield. For example, the western flower thrips (*Frankliniella occidentalis*) are native to North America, but have spread to Europe, Australia and South America. They target over five hundred host plants, including fruits (e.g., grape, strawberry), vegetables (e.g., curcubits, pepper), herbaceous ornamental crops (e.g., impatiens, petunia) and shrubs and trees (e.g., rose, stone fruit). Certain genera (*Frankliniella* and *Thrips*) transmit viruses, particularly tospoviruses (for example, the tomato spotted wilt virus and the impatiens necrotic spot virus), which are considered among the most damaging of plant pathogens.

Although thrips typically inhabit plants, environments of water and high moisture are attractive, providing protection during drought or plant dormancy, and prime reproductive ground for the pupal stage. Such areas include, for example, well irrigated lawns, flower beds, gardens, pine straw, wood chips, grass, thatch, soil, leaf litter, mulch, decomposing material, pool areas, clogged gutters, and areas around garden hoses and water spickets. The life cycle is extremely rapid (two weeks), with eggs being initially laid on plant tissue. Hatched young immediately feed on the plant for about a week, after which some may develop wings, fly off the plant or crawl down to the ground to pupate into fully mature, reproductive adults. Since a few thrips may generate thousands, it is desirable to eradicate developing populations.

Although they do not feed on blood, thrips may bite humans and animals to feed on epidermal lymph, causing thysanoptera dermatitis. During hot, dry weather or as host plants become depleted of vital fluids, thrips are attracted to humans due to their perspiration. Thrips in the pupa stage will readily target humans upon hatching. Once in the home, thrips lay eggs and reproduce in potted plants having water collectors, and humans and pets become targets for feeding. Repellants such as deet and citronella lotion may be useful; however, targeting nest locations before thrips populate is a more feasible option.

The ability of the composition of the present invention to eradicate insects of the order Thysanoptera was determined and compared with the insecticidal activity of Thiodan® WP (Example 2). This commercial insecticide includes endosulfan, a neurotoxin and endocrine disruptor which is highly toxic to humans, pets and wildlife, has a high potential for bioaccumulation and environmental contamination, and has been banned in Europe. The problem with current commercial products such as Thiodan® WP resides in their toxicity, thus limiting their use. The results (FIG. 3) demonstrate that both the exemplary formulation "ARC1004" at the 2.0× rate and Thiodan® WP display similar activity against adult western flower thrips (*Frankliniella occidentalis*). However, the composition of the present invention exhibits a significant advantage over commercial insecticides in being nontoxic to humans, pets and wildlife, and being easily manufactured using standard techniques well known in the art.

Although a narrow host range may be advantageous in targeting a specific insect, limited targeting reduces the use of such products. Multiple insects are associated with animals, on crops or other infested areas. It will be appreciated that a broad spectrum insecticide will eradicate multiple insects at one time, providing a cost-effective and efficient alternative. Expansion of the host range of an insecticide is thus beneficial.

In one embodiment, the composition of the invention may be used against insects of the Order Thysanoptera which includes Thripidae (herbivores including pests such as the flower thrips); Phlaeothripidae (tube-tailed thrips, pest species); Heterothripidae (tree thrips); Aeolothripidae (predaceous species); and Merothripidae (jumping thrips). In one embodiment, the composition is effective against Thripidae. In one embodiment, the composition is effective against the Phlaeothripidae. In one embodiment, the composition is effective against the genera *Frankliniella*. In one embodiment, the composition is effective against western flower thrips (*Frankliniella occidentalis*). The composition is potent against both adult and immature insects.

The composition of the invention is particularly useful for protecting growing and harvested plants including, but not limited to, fruits (e.g., grape, strawberry, blueberry, citrus), vegetables (e.g., curcubits, pepper, avocado, beans, garlic, onion, peas, leeks, cabbage, tomato), herbaceous ornamental plants (e.g., impatiens, petunia, chrysanthemums, poinsettia, gladiolus, privet and honeysuckle), shrubs and trees (e.g., rose, stone fruit), and crops (e.g., wheat, barley, corn, cotton, hay grasses).

EXAMPLES

The following examples are intended to exemplify the claimed invention, and not to limit the claimed invention in any manner.

Example 1

In Vitro Tests

In an experiment, combinations of dormant oil, cinnamon oil, and clove oil, with and without an emulsifier, were tested against adult western flower thrips. The cinnamon oil comprised 83% cinnamaldehyde, 10.84% eugenol with other minor components including 2% trans-caryophyllene and 1.03% (−)-caryophyllene oxide. The following combinations were tested:

| Combination | Components | | | |
|---|---|---|---|---|
| A + B | 0.6% dormant oil | 0.2% cinnamon oil | | |
| A + B + C | 0.6% dormant oil | 0.2% cinnamon oil | 0.1% clove oil | |
| S1 + A + B | 0.6% dormant oil | 0.2% cinnamon oil | | 0.2% PSFA |
| S2 + A + B | 0.6% dormant oil | 0.2% cinnamon oil | | 0.725% PSFA |
| S3 + A + B | 0.6% dormant oil | 0.2% cinnamon oil | | 1.25% PSFA |
| S1 + A + B + C | 0.6% dormant oil | 0.2% cinnamon oil | 0.1% clove oil | 0.2% PSFA |
| S2 + A + B + C | 0.6% dormant oil | 0.2% cinnamon oil | 0.1% clove oil | 0.725% PSFA |
| S3 + A + B + C | 0.6% dormant oil | 0.2% cinnamon oil | 0.1% clove oil | 1.25% PSFA | where S1 = 0.2% PSFA, S2 = 0.725% PSFA, S3 = 1.25% PSFA, and A = 0.6% dormant oil, B = 0.2% cinnamon oil (83% cinnamaldehyde and 10.84% eugenol), and C = 0.1% clove oil (76.1% eugenol). Water was used as a control.

Test combinations were mixed with water and applied directly to test insects, which were anaesthetized using carbon dioxide and placed in a test arena comprised of a 3.5 cm tissue culture dish with a Whatman No. 1 filter paper moistened with 450 microliters of distilled water at the bottom. 400 microliters of test solution was applied to each of 5 test arenas containing 5 test insects each. Test arenas were maintained at 22° C. and 41% RH on a 16:8 light:dark regime. Mortality was assessed 24 hours post-treatment. Each experiment was replicated 3 times.

As may be seen in FIG. 1, thrips mortality was significantly enhanced by the addition of an emulsifier over the same combination without an emulsifier. The combination of dormant oil, cinnamon oil and clove oil had insecticidal activity only slightly higher than that of dormant oil by itself. However, the addition of an emulsifier in increasing concentration resulted in greater insect mortality.

Example 2

Greenhouse Trials 100 female and 20 male western flower thrips from a laboratory culture were placed on poinsettia plants in 10 cm pots. Each plant was enclosed in a nylon sleeve. The plants were left for 24 hours in a greenhouse before treatment with a test composition ARC1004, a registered insecticide Thiodan® WP (Hoechst Schering AgrEvo GmbH) as an industry standard, and water. Five plants each were assigned to a water control, the industry standard, and ARC1004 at 0.5×, 1.0×, 1.5× and 2.0× rates. ARC1004 had the following composition:

| Ingredient | Rate | | | |
|---|---|---|---|---|
| | 0.5× | 1.0× | 1.5× | 2.0× |
| mineral oil | 0.60% | 1.20% | 1.80% | 2.40% |
| clove oil | 0.05% | 0.10% | 0.15% | 0.20% |
| cinnamon oil | 0.10% | 0.20% | 0.30% | 0.40% |
| PSFA | 0.13% | 0.25% | 0.38% | 0.50% |

For treatment, the plants were removed one at a time from their sleeves, and the products were applied by using a hand-operated sprayer until runoff from all sides. Any thrips which escaped from this process were counted and destroyed. The plant was then re-sleeved and placed on a greenhouse bench for 24 hours before counting surviving thrips. Thrips were counted by exposing the plant to carbon dioxide for 15 seconds, removing the sleeve, holding the plant horizontally over a white plastic basin, and tapping the plant four times, rotating it through 90° between each tap. Thrips were collected and counted with an aspirator, the four taps repeated, and the two counts were summed. Preliminary tests with unsprayed plants indicated this method recovered over 70% of live thrips on the plants. Mortality was calculated for each plant by the Henderson-Tilton formula using the mean pre-treatment and post-treatment numbers on the water control.

Figure 2:
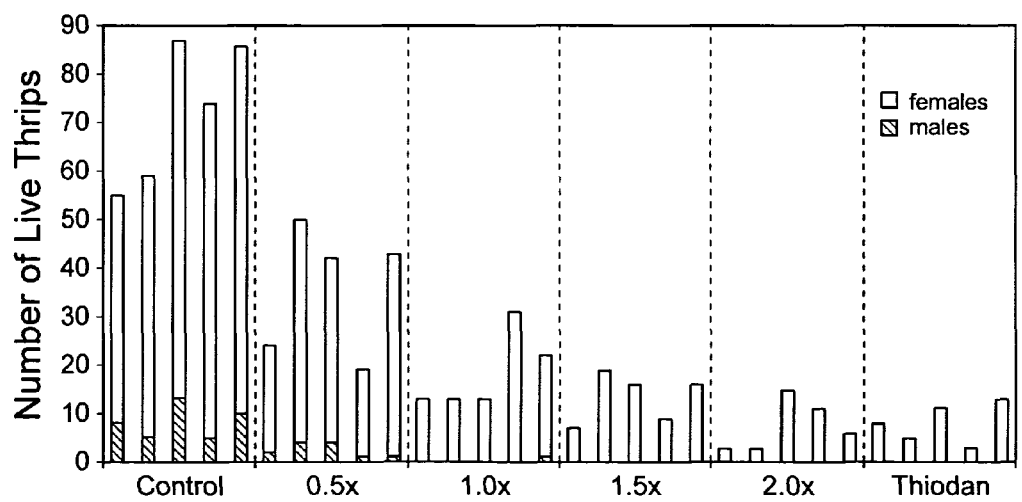
FIG. 2 is a graph showing efficacy of one embodiment of the invention at four different rates against adult western flower thrips, compared with a water control and an industry standard insecticide.
Figure 3:
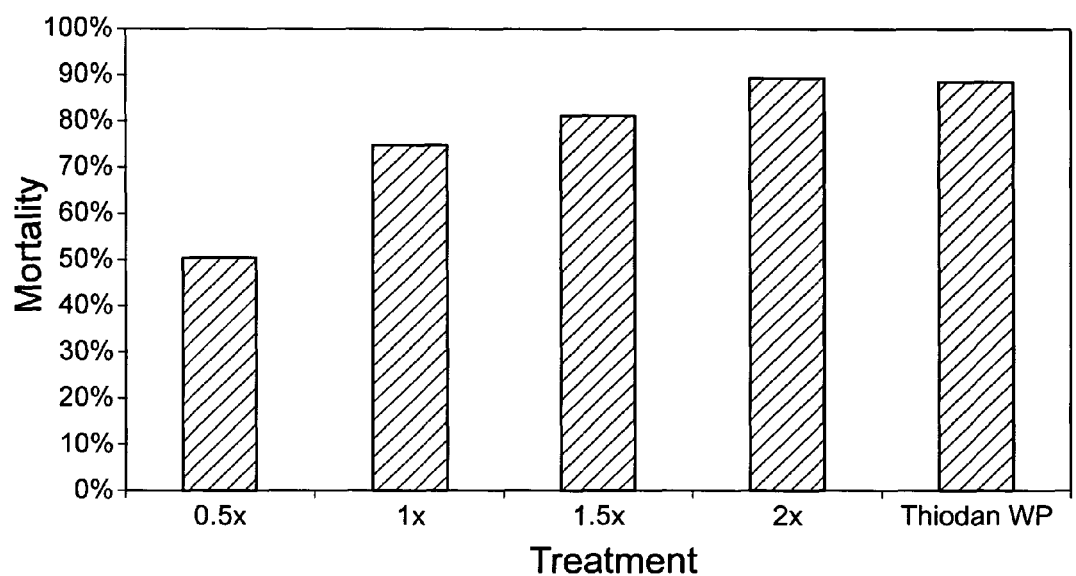
FIG. 3 is a graph showing mean mortality of thrips calculated from the results shown in FIG. 2.

The number of live thrips in each case is shown in FIG. 2. Mean mortality rates calculated from the data in FIG. 2 are shown in FIG. 3. ARC1004 at the 2.0× rate gave a mean mortality of 89.5%, which was virtually identical to the rate of 88.8% for Thiodan. Treatment with 1.0× and 1.5× resulted in mean mortality in excess of 70%.

Example 3

Several formulations were prepared by mixing together the following components in the proportions indicated:
(a) 0.1-2.0% of an emulsifier;
(b) 0.1-1.8% horticultural oil;
(c) 0.1-1.2% cinnamaldehyde; and
(d) 0.1-1.2% eugenol.
The emulsifier comprised potassium salts of fatty acids. The horticultural oil comprised dormant oil in one formulation, and mineral oil in another formulation.

Example 4

Several formulations were prepared by mixing together the following components in the proportions indicated:
(a) 0.2-1.50% of an emulsifier;
(b) 0.2-0.3% horticultural oil;
(c) 0.1-0.2% cinnamaldehyde; and
(d) 0.1-0.2% eugenol.
The emulsifier comprised potassium salts of fatty acids. The horticultural oil comprised dormant oil in one formulation, and mineral oil in another formulation.

Example 5

A stock formulation was prepared and diluted with distilled water to provide the composition of Example 3.

What is claimed is:

1. An insecticidal composition consisting essentially of ingredients which are generally regarded as safe, including:
    (a) 0.1-2.0% of an emulsifier comprising potassium salts of fatty acids;
    (b) 0.1-2.4% horticultural oil;
    (c) 0.1-1.2% cinnamaldehyde; and
    (d) 0.1-1.2% eugenol.

2. The composition of claim 1 wherein the horticultural oil comprises dormant oil.

3. The composition of claim 1 wherein the horticultural oil comprises mineral oil.

4. The composition of claim 1 consisting essentially of:
    (a) 0.2-1.50% of an emulsifier;
    (b) 0.2-1.20% horticultural oil;
    (c) 0.1-0.2% cinnamaldehyde; and
    (d) 0.1-0.2% eugenol.

5. A concentrated insecticidal composition having the composition of claim 1 upon dilution with water.

6. A method for controlling or eradicating an insect comprising the steps of preparing a composition in accordance with claim 1
    and contacting the insect with an insecticidally effective amount of the composition or applying an insecticidally effective amount of the composition to an infested area.

7. The method of claim 6, wherein the horticultural oil comprises dormant oil or mineral oil.

8. The method of claim 6, wherein the composition consists essentially of:
    (a) 0.2-1.50% of an emulsifier;
    (b) 0.2-1.20% horticultural oil;
    (c) 0.1-0.2% cinnamaldehyde; and
    (d) 0.1-0.2% eugenol.

9. The method of claim 6, wherein the insect is an immature or adult insect selected from Order Thysanoptera or Order Homoptera.

10. The method of claim 9, wherein the insect is selected from Thripidae or Phlaeothripidae.

11. The method of claim 10, wherein the insect is the western flower thrips.

12. The method of claim 6, wherein the composition is prepared in the form of a liquid or suspension.

13. The composition of claim 1 including 0.2-0.6% cinnamaldehyde.

14. The method of claim 6 wherein the composition includes 0.2-0.6% cinnamaldehyde.

* * * * *